United States Patent [19]

Settler

[11] Patent Number: 4,681,116

[45] Date of Patent: Jul. 21, 1987

[54] ANTIMONY ELECTRODE ASSEMBLY AND METHOD OF MANUFACTURE, AND USE THEREOF

[76] Inventor: Bert Settler, 723 Queenston Street, Winnipeg, Manitoba, Canada, R3N 0X8

[21] Appl. No.: 796,704

[22] Filed: Nov. 12, 1985

[30] Foreign Application Priority Data

Nov. 12, 1984 [GB] United Kingdom .................. 8428543

[51] Int. Cl.$^4$ ............................................... A61B 5/00
[52] U.S. Cl. ..................................................... 128/635
[58] Field of Search ................ 128/635; 204/403, 433, 204/435

[56] References Cited

U.S. PATENT DOCUMENTS

| | | | |
|---|---|---|---|
| 2,168,867 | 8/1939 | George | 128/635 |
| 2,387,727 | 10/1945 | Godshalk | 204/435 |
| 2,684,938 | 7/1954 | Mantzell | 204/433 X |
| 3,123,067 | 3/1964 | Clark, Jr. | 128/635 |
| 3,671,414 | 6/1972 | Grubb | 204/433 X |
| 3,806,439 | 4/1974 | Light et al. | 204/435 |
| 4,119,498 | 10/1978 | Edwell et al. | 128/635 X |
| 4,128,468 | 12/1978 | Bukamier | 204/435 X |
| 4,561,963 | 12/1985 | Owen et al. | 128/635 X |
| 4,565,666 | 1/1986 | Cahalan et al. | 128/635 X |

FOREIGN PATENT DOCUMENTS

| | | | |
|---|---|---|---|
| 987388 | 4/1976 | Canada. | |
| 2477716 | 9/1981 | France | 204/435 |

Primary Examiner—Lee S. Cohen
Attorney, Agent, or Firm—Stanley G. Ade

[57] ABSTRACT

An antimony electrode for pH measurement is formed with a convex, very smooth tip and sealed within a flexible plastic sheath with just the tip exposed. A reference electrode is provided either separately or in conjunction with the antimony electrode, the reference electrode being sealed within a plastic tube surrounded by an electrolyte. One end of the reference electrode is operatively connected through one end of the tube, to a conductor cable. The other end of the reference electrode terminates spaced internally from the other end of the tube and a plug closes this other end. This plug is formed from a material such as wood, which is saturated with electrolyte that forms an electrolytic connection between the exposed end of the plug of the electrolyte within the tube and hence with the reference electrode in the tube.

5 Claims, 9 Drawing Figures

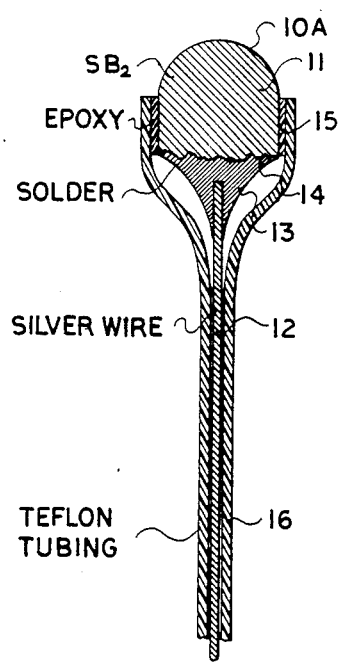
FIG.1
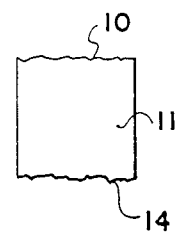
FIG. 2
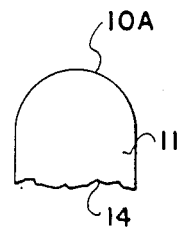
FIG.3
|     |    | 1ST TEST |   | 2ND TEST |   | 3RD TEST |   | 4TH TEST |   |
|-----|----|---|---|-----|-----|-----|-----|-----|-----|
|     | PH | 3 | 7 | 3   | 7   | 3   | 7   | 3   | 7   |
| (A) | PH | 3 | 7 | 3.2 | 7.2 | 3.4 | 6.8 | 3.3 | 7.2 |
| (B) | PH | 3 | 7 | 3.1 | 7.2 | 3.2 | 7.1 | 3   | 7.3 |
| (C) | PH | 3 | 7 | 3   | 7   | 3   | 7   | 3   | 7   |
FIG.4

ANTIMONY ELECTRODE ASSEMBLY AND METHOD OF MANUFACTURE, AND USE THEREOF

BACKGROUND OF THE INVENTION

This invention relates to new and useful improvements in the manufacture and use of antimony electrode assemblies for the measurement of pH either orally or internally and with or without a separate or integral reference electrode. However, it will of course be appreciated that it can be used to measure pH in other environments if desired. One method of manufacture of antimony electrode assemblies is described in Canadian Pat. No. 987,388 dated Apr. 13, 1976.

This Canadian Patent discloses the method of forming the antimony rod from which the relatively small pieces are cut or otherwise detached from the rod.

One of these pieces is then soldered in end to end relationship, by one end thereof to one end of a length of silver wire and relatively hard plastic is used to coat all of the rod, the solder junction and part of the silver wire leaving the distal tip of the rod exposed and it is this tip that is used to measure pH.

However, it has been found that this exposed tip is relatively rough thus disturbing the pH readings to the extent that they fluctuate depending upon the circumstances. Furthermore, covering the junction between the rod and wire, and a portion of the wire has been found to weaken rather than strengthen the junction inasmuch as if a bend does occur in the wire above the lower end of the relatively hard plastic, the plastic tends to crack away relatively easily.

SUMMARY OF THE INVENTION

The present invention teaches, among other things, improvements in the method of manufacture which contemplates grinding the end of the antimony rod which will remain exposed, to a convex substantially hemispherical configuration and then highly polishing this convex surface so that it is substantially crystallographically undisturbed. The area around the tip of the antimony rod is then coated with an epoxy resin which can be cured to a relatively hard coating and this coating may extend either part way along the rod or all of the way along the rod excluding the soldered joint at the other end of the of the rod and any of the silver wire attached to the other end by the soldered joint.

The electrode and all or part of the silver wire is then inserted into a flexible TEFLON (T.M.) tube which shields and insulates the antimony electrode and the silver wires gives the necessary strength to the junction between the electrode and the wire and permits the wire to be manipulated within limits so that it can be used in the variety of circumstances including esophageal pH monitoring.

In accordance with the invention there is provided a method of manufacturing a pH electrode from a length of antimony rod consisting of the steps of;

(a) grinding the distal end of the antimony rod into a convex configuration, (b) highly polishing said distal end as close as possible to a single, one place crystal face, (c) securing a conducting wire by one end thereof to the other end of said antimony rod, (d) covering part of said rod with a relatively hard epoxy resin but leaving the convex distal end bare, (e) covering the antimony rod, the junction of the rod with the conducting wire and at least part of the conducting wire, with a flexible plastic tubing up to but not including the convex distal end of said rod, and then (f) sealing the tubing to the antimony rod at least around the bare convex distal end, against the ingress of contaminants.

In accordance with another aspect of the invention there is provided an antimony electrode for pH measurement comprising in combination a relatively short length of antimony rod secured by one end thereof, as by soldering, to one end of a conducting wire, the distal end of said rod being convex and substantially hemispherical and having a highly polished surface approaching a single, one plane crystal face, a relatively hard epoxy resin covering at least part of the length of said rod but with the distal end remaining exposed, a flexible plastic tube surrounding said rod, the junction of said rod with said conducting wire, and at least part of said conducting wire, with said distal end of said rod remaining exposed, said portion of said plastic tube adjacent said distal end of said rod being in sealing relationship around said rod to prevent ingress of contaminants.

In accordance with a further aspect of the invention there is provided a reference electrode assembly comprising in combination a length of tubing, an electrolyte permeated plug in one end of said tubing, a reference electrode within said tubing and operatively extending from the other end thereof in sealing relationship therewith, and an electrolyte within said tubing surrounding a portion of said reference electrode within said tubing, said electrolyte permeated plug operatively connecting the distal end of said plug to the electrolyte within said tubing.

With the foregoing in view, and other advantages as will become apparent to those skilled in the art to which this invention relates as this specification proceeds, the invention is herein described by reference to the accompanying drawings forming a part hereof, which includes a description of the best mode known to the applicant and of the preferred typical embodiment of the principles of the present invention, in which:

DESCRIPTION OF THE DRAWINGS

FIG. 1 is a fragmentary cross-sectional schematic view of the assembly enlarged in size for clarity.

FIG. 2 is an enlarged side elevation of a conventional antimony electrode piece.

FIG. 3 is a view similar to FIG. 2 but showing the electrode in side elevation according to the invention.

FIG. 4 is a chart showing the comparative tests between a pair of standard pH samples and three electrodes having various distal end configurations and/or finishes.

DETAILED DESCRIPTION

Figure 5:
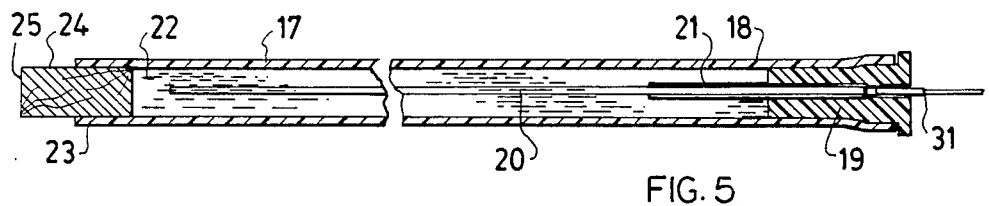
FIG. 5 is a schematic side elevation of the reference electrode assembly per se.

Proceeding therefore to describe the invention in detail, the antimony, which is 99.9% pure, is broken out of a glass encased rod in a manner similar to that described in the above identified Canadian Patent. The diameter of the rod is approximately between 1-2 mm. The rod is then broken or cut into small pieces approximately 2-3 mm long. These pieces, when cut, have very rugged ends similar to that shown in FIG. 2. One end 10 of the antimony piece of rod 11 is then ground to a convex substantially hemispherical configuration 10A as shown in FIG. 3 making it relatively easy to clean before use. This convex surface 10A is then highly polished with a fine pumice.

This surface 10A is then again polished to an extremely high finish with a special metallurgical polish such as JEM-sparkle (TM) a tumbling charge repolish manufactured by Lortoner Inc., Seattle, Wash., U.S.A., 98107. This is used in order to prevent any distortion of subsequent results due to polish residue lodging in micro-crevices which might occur if a polish such as Jewellers Rouge is used. Metallurgical polish is inert in this respect.

The purpose of the polishing is to bring this exposed surface as close as possible to a single, one plane crystal face that is exposed to the liquid or surface being tested.

Measuring and comparing the ground and polished surfaces one with the other may be accomplished by using a Reflexometer in order to confirm what can be seen with the naked eye or by magnification. This enables replication to take place within design parameters.

A silver wire 12 is then soldered as at 13 to the other end 14 of the antimony electrode 11 in end to end or butt-joint relationship. Relatively hard epoxy resin 15 is then used to cover all or part of the electrode 15 except the face 10A and flexible TEFLON (T.M.) tubing 16 covers the assembly and acts as reinforcement and as an insulator. As will hereinafter be described in detail, the next step is to completely seal the area around the polished tip of the electrode in order to prevent any leakage of liquid along the sides and between the sheath and the electrode which of course would cause readings to be erratic.

A suitable epoxy for use in coating all or part of the rod 11 is an epoxy manufactured by Hysal division of the Dexter Corporation and listed as Hysal IC has been found to be eminently successful in bonding to the sides of the electrode in order to prevent leakage. This product is factory pre-mixed in a vacuum and placed in ICC vials. The vials are fast frozen and maintained in a frozen condition during transportation and storage. When ready for use, the vials are individually thawed and the epoxy is applied to the total surface of the electrode that has not been polished. In other words all of the electrode with the exception of the polished one end may be coated and the electrode is then placed in an oven for two hours at 60° C. in order that curing may take place. This IC epoxy is non-toxic when cured and has been U.S.D.A. approved.

It should be understood that only the polished exposed end of the antimony electrode is used in the monitoring process. The rest of the exposed sides are coated with this relatively rigid epoxy 15 although of course full length coverage is not essential.

I have found that four different stages of applying the epoxy 15 may be used efficiently.

(1) Epoxy applied to cover 100% of the electrode and the solder up to but not including the silver wire attached thereto, leaving the polished face exposed.

(2) Epoxy applied to cover 100% of the electrode only, once again with the exception of the polished end.

(3) Epoxy applied to cover 75% of the antimony electrode with the polished face being exposed.

(4) Epoxy applied to cover 100% of the antimony electrode and 75% of the solder, once again leaving the polished face exposed.

The above are exemplary only and may of course be varied, once again depending upon design parameters.

However, whichever degree of covering with the relatively rigid epoxy 15 is used, nevertheless it will be understood that any exposed surface of the electrode, excepting the polished tip or face, together with exposed solder and attached silver wire must be shielded electrically and this is accomplished by means of inserting the assembly into a length of treated, clear extruded TEFLON (T.M.) tubing such as Cole-Flex TT-250/22. AMS-3655.

This tubing has an inside diameter of 0.027 inches with a wall thickness of 0.010 inches and an outside diameter of 0.047 inches. However other dimensioned tubing may of course be utilized.

The end of this tubing engaging around the antimony electrode portion of the assembly adjacent the polished end surface, must be sealed to the epoxy 15 in order to prevent contamination occurring between the tubing and the epoxy. Because of the difficulty of sealing TEFLON (T.M.) tubing, the end of the TEFLON (T.M.) tubing must be neutralized before adhesively securing same to the electrode.

The exposed inner and outer surfaces of the TEFLON (T.M.) tubing approximately 3 to 4 inches back from the end to be attached, are treated as follows in small individual beakers although other containers may of course be used.

(a) Flush and dip in Ethyl Acetate, then air dry (Fisher Scientific E14573952);

(b) Flush and dip into a solution until the tubing turns dark brown (immersed for 50 to 60 seconds) and then air dry (Chemgrip Treating Agent by Chemplast Inc.);

(c) Clean and flush in Acetate;

(d) Flush and rinse in a solution of hot water and detergent;

(e) Air dry.

In the final assembly of the electrode, the silver wire with the antimony electrode attached by solder, is pulled through one end of the treated TEFLON (T.M.) tubing. A small quantity of 0151 Hysal Epoxy or other equivalent adhesive is applied to the end tip of the TEFLON (T.M.) tubing that has been treated, just before it is finally pulled into position with this treated end substantially flush with the exposed polished end of the electrode as clearly shown in FIG. 1. The completed unit is then left to air dry at room temperature of 70° F., for approximately 12 hours.

FIG. 4 shows a chart which indicates:

(a) testing of an antimony electrode before grinding.

(b) the test after grinding to a concave shape;

(c) and testing after two polished finishes as hereinbefore described.

Two pH sources were used, namely, pH3 and pH7 and four tests were taken with the results shown on the chart, it being understood that the electrodes were cleaned between each use. It will be noted that the highly polished electrodes (c) prove far superior to the conventional electrode shown in (a).

Conventional electrodes do not have a highly polished convex exposed face but a rough surface or sometimes, a ground convex shape which is not polished so that variations in pH measurements occur.

Some conventional electrodes use a relatively hard epoxy which covers all of the antimony electrode with the exception of the exposed face, all of the solder and a small portion of the silver wire attached to the electrode by the solder. Often, the balance of the silver wire has also been epoxied and shielded with a softer epoxy which is also subject to breaking when bent.

The present assembly overcomes all of the disadvantages inherent with conventional assemblies and in addition provides a highly polished exposed antimony electrode surface which enables extremely accurate measurements of pH to be taken as shown in (c) on the chart shown in FIG. 4.

Dealing next with FIGS. 5 through 9, FIG. 5 illustrates a reference electrode for use with the electrode assembly described and illustrated in FIGS. 1 through 3.

It consists of a length of plastic tubing 17 which is preferably formed from an intramedic nonradiopaque polyethylene material being sealed at one end 18 by means of a connector such as a tip jack 19 to which may be connected a connecting conductor or cable (not illustrated).

Situated within the tubing is a length of silver wire 20 sealable and operatively connected to the tip jack 19 by one end thereof and sealed by an epoxy resin seal 21 surrounding the first portion of the silver wire 20.

The silver wire is coated with silver chloride by dipping the wire into a supply of molten silver chloride powder thus producing what is known as a silver silver chloride conductor.

Surrounding this conductor and filling the tube 17 is an electrolyte in the form of a gel formed from potassium or sodium chloride with potassium chloride being the preferred electrolyte. Redux Cream manufactured by Hewlitt Packard is a suitable electrolytic gel. Reference character 22 illustrates this electrolyte within the tube 17 and it should be noted that the electrode 20 terminates spaced from the other end 23 of the tube 17.

This said other end is sealed by means of a plug 24 frictionally and sealably engaged therein with the distal end 25 extending from the end 23 of the tube and this plug is saturated in an electrolyte so that it is electrolytically connected between the distal end 25 and the gel 22 within the tube 17.

In the present embodiment, a wooden plug is utilized manufactured from pine which is saturated in a concentrated solution of potassium or sodium chloride and a mixture of distilled water for a period of approximately 18 days to insure complete impregnation of the plug with the electrolyte solution.

This enables the electrodes 20 to indicate the pH contacted by the distal end portion 25 of the plug 24 and to convey same via the cable extending from the tip jack 19 to suitable instrumentation (not illustrated).

The advantages over conventional reference electrodes is that the liquid junction between the sample and the electrolyte is completely isolated so that contamination of the sample with the electrolyte during measurements does not take place. Conventionally, such electrolytes utilize a drip method to insure the necessary conduction whereas the present reference electrode is extremely rugged and does not contaminate and can be used in various environments where pH measurements are required without contamination.

Figure 6:
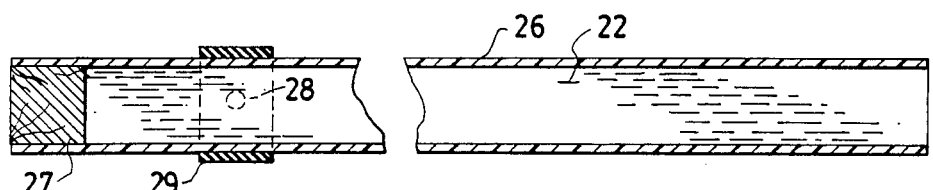
FIG. 6 is a schematic side elevation of a storage tube for the reference electrode of FIG. 5.

It will of course be appreciated that it is necessary to maintain the plug 24 in the electrolytic conducting relationship with the electolyte 22 within the tubing and reference should be made to FIG. 6 which shows a storage tube 26 consisting of a length of polyethylene tubing or the like having a plug 27 at one end thereof sealing off this one end.

This tube is filled with an electrolyte gel solution including either potassium or sodium chloride and in this connection a vent hole 28 may be formed through the wall of the tube adjacent plug 27 to ensure complete filling of the tube. This hole or aperture 28 may be sealed with a small rubber band 29 or the equivalent thereof. When storing the reference electrode or transporting same, the reference electrode is inserted into the tube with the distal end 25 of the plug remaining completely immersed within the electrolyte solution and maintaining the saturation of the plug for efficient conductivity between the distal end 25 and the electrolytes 22 within the reference electrode assembly.

When ready for use, the reference electrode assembly is withdrawn from the tube 26, the tip 25 is dried and dipped in distilled water and then dried again and is then ready for use.

It should be noted that the tip jack 19 is soldered to the end of the silver silver chloride wire or electrode and is then frictionally engaged within the end of the tubing 17. It is sealed on the outside and then treated with an accelerator which increases gap filling abilities and minimizes adhesive migration from the bond areas. The electrolyte cream or gel is then injected into the tubing 17 from the other end thereof to overflowing and then the saturated plug 24 is forced into the end of the tubing and secured by an epoxy resin or the like around the area where the peg extends from the end of the tubing. Once again a bonding and accelerator may be applied to prevent adhesive migration.

Figure 7:
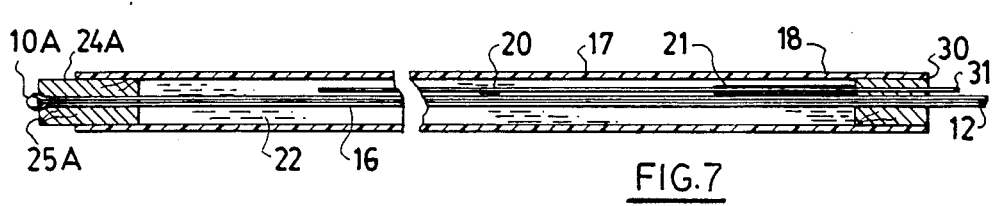
FIG. 7 is a schematic side elevation of the reference electrode in combination with the antimony electrode assembly.
Figure 8:
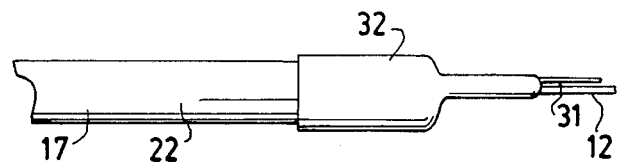
FIG. 8 is an enlarged fragmentary side elevation of the right hand end of the assembly shown in FIG. 7.

FIGS. 7 and 8 show a reference electrode in combination with the antimony electrode assembly previously described and, where applicable, similar reference characters have been used.

The tube 17 is of similar construction to that described in FIG. 5 and the electrolytically saturated plug 24A is similar with the exception that it is drilled longitudinally to sealably receive the distal end of the electrode assembly illustrated in FIG. 1 with the exposed tip 10A of the antimony electrode extending beyond the distal end 25A of the plug 24A as clearly illustrated.

The electrode wire 12 encased within the TEFLON (T.M.) tubing 16 extends through the gel 22 within the tubing parallel to the reference electrode 20 which is also within the tubing 17. The plastic tubing 16 and wire 12 of the antimony electrode extend through a plug 30 together with the conductor 31 of the reference electrode and a plastic housing or piece of tubing 32 extends over the end 18 of the tube 17 where the two conductors emerge. The end of the antimony electrode extending through the saturated plug 24A is sealed by epoxy as is the plug 24A where it engages the end 22 of the tubing.

The other end of the tubing is also sealed with epoxy as hereinbefore described with reference to FIG. 5 and the two wires may then be terminated in a conventional cable end connector (not illustrated). Once again, the plug 24A is saturated with an electrolyte and the conductivity and saturation is maintained by storing same in a storage tube as illustrated in FIG. 6 and previously described.

Figure 9:
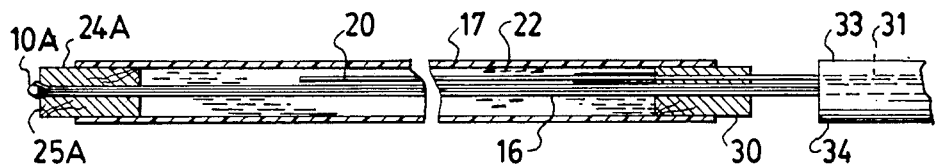
FIG. 9 is a fragmentary, partly schematic side elevation of the combination pH electrode and reference electrode of FIG. 7 but adapted for internal use as in an esophageal electrode assembly.

Finally, reference should be made to FIG. 9 which utilizes the combination reference and antimony electrode assembly of FIG. 7 with the exception that the conductors 12 and 31 are relatively long and covered with an intramedic tubing 33, the end 34 of which is sealably engaged over the end 18 of the tube 17 and with the termination of the conductors being operatively connectible to the necessary meter (not illustrated) with a relatively long length of tubing covering the conductors, the device is suitable particularly for esophageal examination.

Again the combination electrode should of course be stored in a storage tube as in FIG. 6, when not in use.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. An antimony electrode for pH measurement comprising in combination a relatively short length of antimony rod having an inner end and an outer or distal end secured by the inner end thereof, as by soldering to one end of a flexible conducting wire, the distal end of said rod being convex and substantially hemispherical and having a highly polished surface approaching a single, one plane crystal face, a relatively hard epoxy resin covering at least part of the length of said rod but with the distal end remaining exposed, a flexible plastic tube surrounding said rod the junction of said rod with said conducting wire and at least part of said conducting wire, with said distal end of said rod remaining exposed and a sealant between said portion of said plastic tube adjacent said distal end of said rod and said distal end of said rod thereby providing a sealing relationship of said plastic tube around said rod to prevent ingress of contaminants.

2. A pH sensor assembly comprising in combination an antimony electrode, said antimony electrode including a relatively short length of antimony rod having an inner end and an outer or distal end, secured by the inner end thereof, as by soldering, to one end of a flexible conducting wire, the distal end of said rod being convex and substantially hemispherical and having a highly polished surface approaching a single, one plane crystal face, a relatively hard epoxy resin covering at least part of the length of said rod but with the distal end remaining exposed, a flexible plastic tube surrounding said rod, the junction of said rod with said conducting wire, and at least part of said conducting wire, with said distal end of said rod remaining exposed, and a sealant between said portion of said plastic tube adjacent said distal end of said rod and said distal end of said rod thereby providing a sealing relationship of said plastic tube around said rod to prevent a length of electrode assembly holding tubing, means mounting the distal end portion of said antimony electrode in one end of said tubing with the distal convex end of said rod exposed, the other end of said antimony electrode operatively extending in sealing relationship through the other end of said tubing, a reference electrode within said tubing, one end of said reference electrode assembly also operatively extending in sealing relationship, through said other end of said tubing and a gel type electrolyte within said tubing and surrounding the portion of at least said reference electrode therewithin, said means mounting the distal end portion of said antimony electrode in one end of said tubing including a liquid-electrolyte-permeated portion extending therethrough and being in electrolytical connection with the electrolyte within said tubing.

3. The combination according to claim 2 in which said electrolyte within said electrode assembly holding tubing comprises a gel consisting of a chloride selected from the group consisting of potassium chloride and sodium chloride.

4. The combination according to claim 3 usable as an esophageal electrode assembly and which includes a conducting wire operatively secured to one end of said reference electrode, said conducting wire of said reference electrode and said conducting wire of said pH antimony electrode extending in sealed relationship from said other end of said electrode assembly holding tubing, a length of intramedic plastic tubing enclosing said conducting wires and being sealed to said other end of said electrode assembly holding tubing, and connecting plug means operatively connected to the other ends of said conducting wires.

5. The combination according to claim 2 usable as an esophageal electrode assembly and which includes a conducting wire operatively secured to one end of said reference electrode, said conducting wire of said reference electrode and said conducting wire of said pH antimony electrode extending in sealed relationship from said other end of said electrode assembly holding tubing, a length of intramedic plastic tubing enclosing said conducting wires and being sealed to said other end of said electrode assembly holding tubing, and connecting plug means operatively connected to the other ends of said conducting wires.

* * * * *